United States Patent
Gwin et al.

(10) Patent No.: US 9,403,110 B2
(45) Date of Patent: Aug. 2, 2016

(54) FILTERS, FILTER ASSEMBLIES, FILTER SYSTEMS AND METHODS FOR IDENTIFYING INSTALLATION OF QUALIFIED FILTER ELEMENTS

(71) Applicant: Cummins Filtration IP, Inc., Columbus, IN (US)

(72) Inventors: Jared M. Gwin, Cookeville, TN (US); Sainath Reddy Racha, Cookeville, TN (US); Gregory D. Shope, Cookeville, TN (US); Yiming Z. Jiang, Cookeville, TN (US)

(73) Assignee: CUMMINS FILTRATION IP, INC., Columbus, IN (US)

( * ) Notice: Subject to any disclaimer, the term of this patent is extended or adjusted under 35 U.S.C. 154(b) by 0 days.

(21) Appl. No.: 14/950,199

(22) Filed: Nov. 24, 2015

(65) Prior Publication Data

US 2016/0074786 A1    Mar. 17, 2016

Related U.S. Application Data

(62) Division of application No. 13/864,694, filed on Apr. 17, 2013, now Pat. No. 9,279,780.

(60) Provisional application No. 61/640,420, filed on Apr. 30, 2012.

(51) Int. Cl.
*G01N 27/02* (2006.01)
*B01D 35/143* (2006.01)
(Continued)

(52) U.S. Cl.
CPC ............ *B01D 35/143* (2013.01); *B01D 36/005* (2013.01); *G01N 27/02* (2013.01); *G01N 27/028* (2013.01); *G01N 27/04* (2013.01); *G01N 27/07* (2013.01); *G01N 33/2847* (2013.01); *B01D 2201/291* (2013.01); *B01D 2201/4046* (2013.01)

(58) Field of Classification Search
CPC ..... G01N 27/02; G01N 27/028; G01N 27/04; G01N 27/07; G01N 33/2847; B01D 35/143; B01D 36/005; B01D 2201/291; B01D 2201/4046
USPC .................................. 324/656, 654, 649, 600
See application file for complete search history.

(56) References Cited

U.S. PATENT DOCUMENTS 3,950,740 A    4/1976    Greene
4,517,547 A    5/1985    Gray et al.
(Continued)

OTHER PUBLICATIONS

International Search Report and Written Opinion in Counterbore International Patent Application No. PCT/US2013/037972, date of mailing Sep. 18, 2013.

*Primary Examiner* — Hoai-An D Nguyen
(74) *Attorney, Agent, or Firm* — Foley & Lardner LLP

(57) ABSTRACT

A filter assembly has a qualified filter element that filters fuel, a filter housing for the qualified filter element and a water-in-fuel sensor that senses presence of water in the filter housing. An electrical resistance of the water-in-fuel sensor changes based upon whether the qualified filter element is installed in the housing. A filter assembly can also have a plurality of magnetic elements disposed on at least one of the filter housing and the qualified filter element. A plurality of wires are disposed on at least the other of the filter housing and the qualified filter element. The control circuit determines that the qualified filter element is installed in the filter housing based on a change in the electrical current in the plurality of wires.

11 Claims, 11 Drawing Sheets

(51) Int. Cl.
  *G01N 27/04* (2006.01)
  *G01N 27/07* (2006.01)
  *G01N 33/28* (2006.01)
  *B01D 36/00* (2006.01)

(56) References Cited

U.S. PATENT DOCUMENTS

| | | |
|---|---|---|
| 4,680,110 A | 7/1987 | Davis |
| 5,587,680 A | 12/1996 | Smith |
| 6,051,144 A | 4/2000 | Clack et al. |
| 6,224,439 B1 | 5/2001 | Sato et al. |
| 6,444,121 B1 | 9/2002 | Maxwell |
| 6,533,926 B2 | 3/2003 | Hawkins et al. |
| 6,537,444 B2 | 3/2003 | Wilberscheid et al. |
| 6,584,768 B1 | 7/2003 | Hecker et al. |
| 6,703,937 B1 * | 3/2004 | Franz et al. ........ B01D 46/0086 340/607 |
| 7,246,717 B2 | 7/2007 | Rodgers et al. |
| 7,615,151 B2 | 11/2009 | Wieczorek et al. |
| 7,850,845 B2 | 12/2010 | Wieczorek et al. |
| 2003/0085180 A1 | 5/2003 | Akins et al. |
| 2003/0136726 A1 | 7/2003 | Gruca |
| 2007/0210008 A1 | 9/2007 | Sprenger et al. |
| 2010/0276352 A1 | 11/2010 | Mendel et al. |
| 2011/0220560 A1 | 9/2011 | Verdegan et al. |
| 2011/0259802 A1 | 10/2011 | Wieczorek et al. |
| 2011/0308395 A1 | 12/2011 | Adams et al. |
| 2012/0234770 A1 | 9/2012 | Goodwin |
| 2013/0031963 A1 | 2/2013 | Ritchie et al. |

* cited by examiner

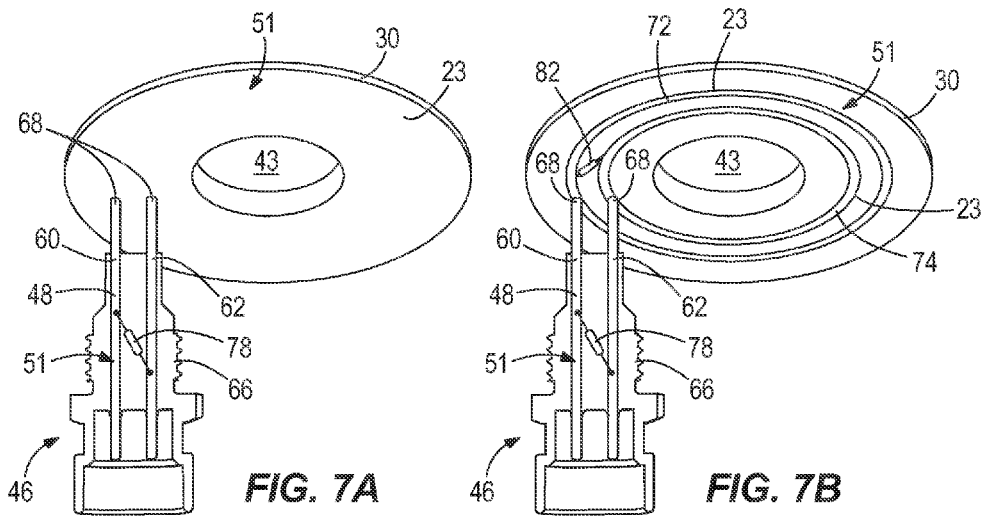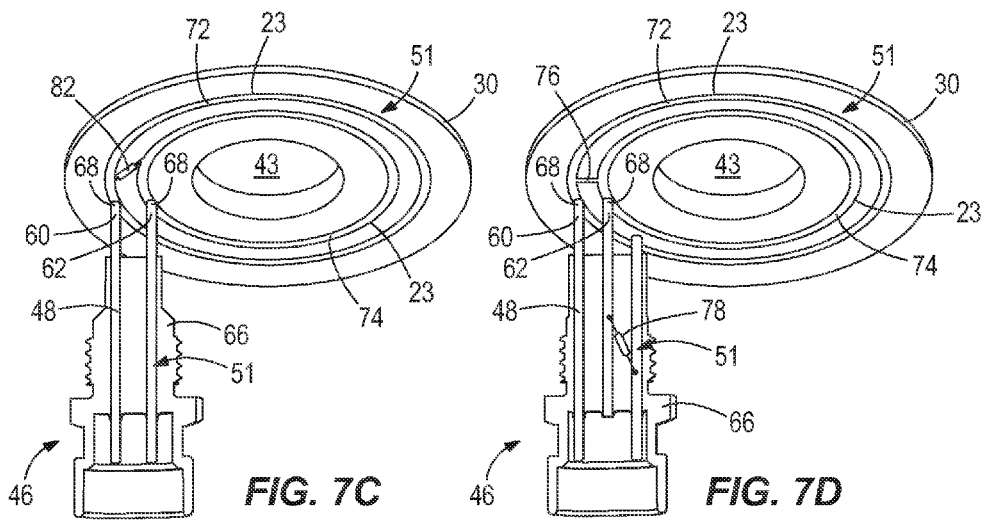

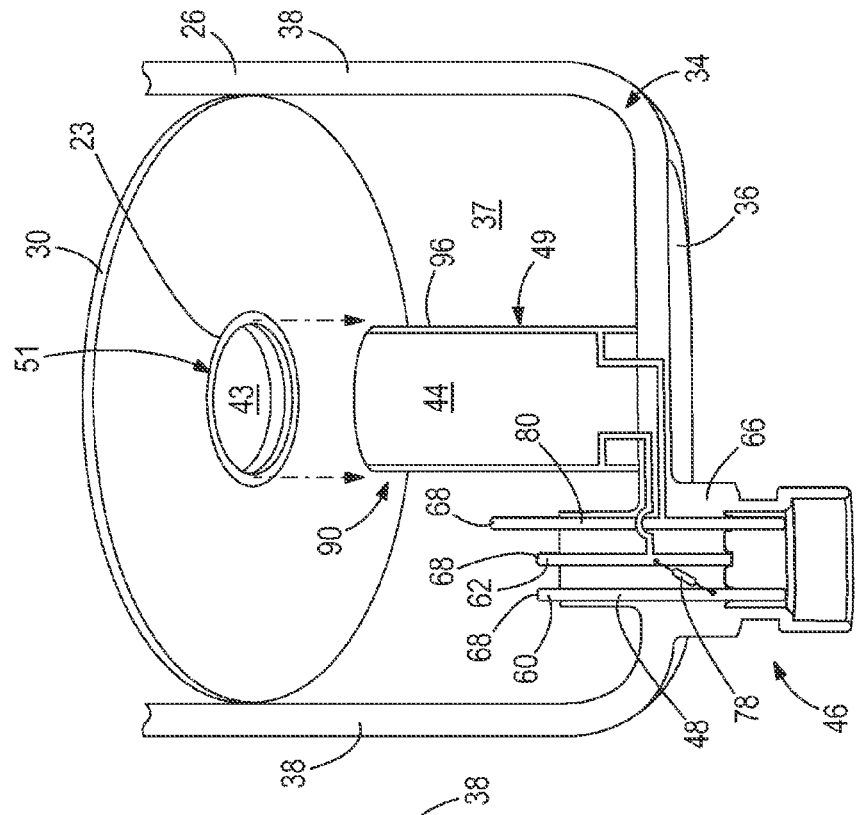
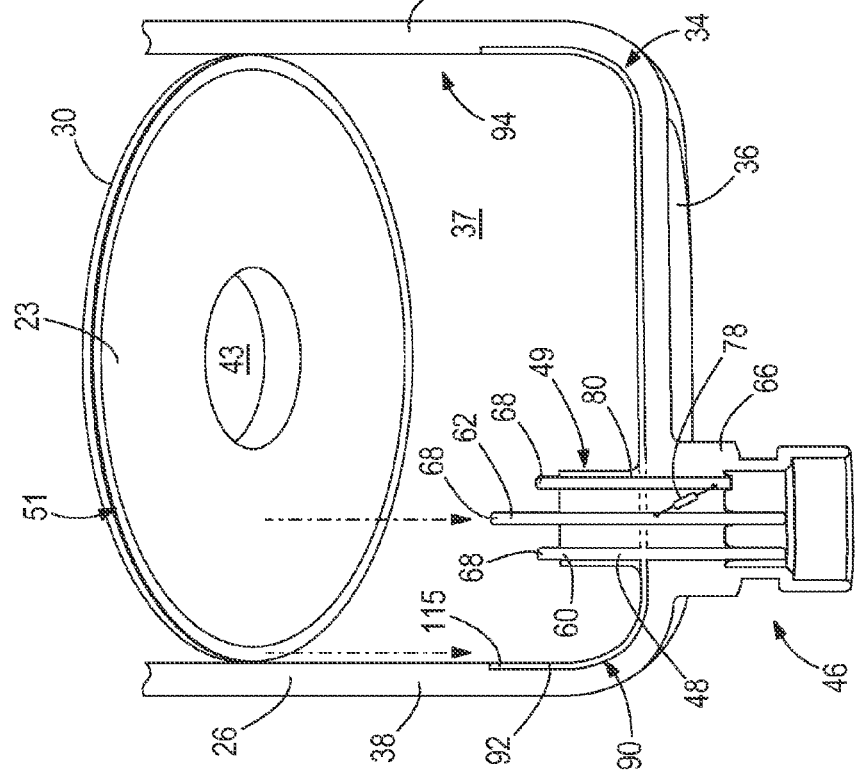
FIG. 8A
FIG. 8B

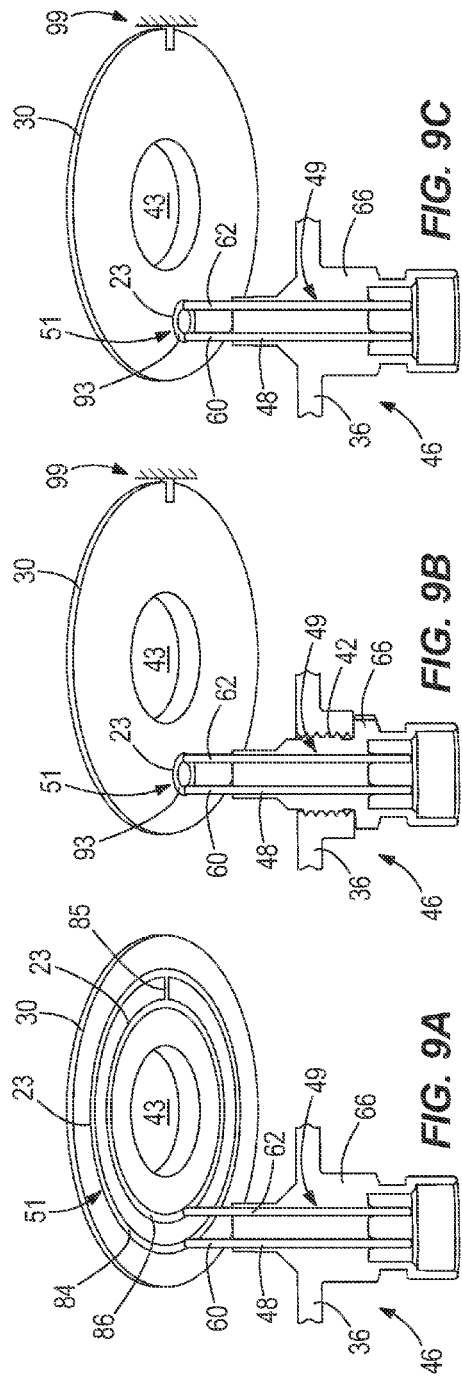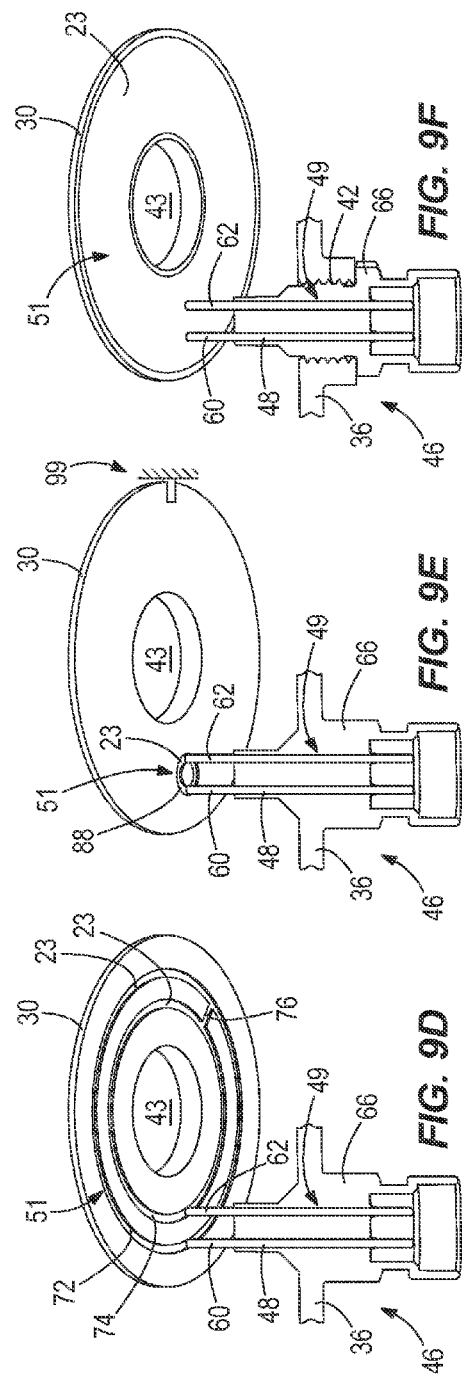

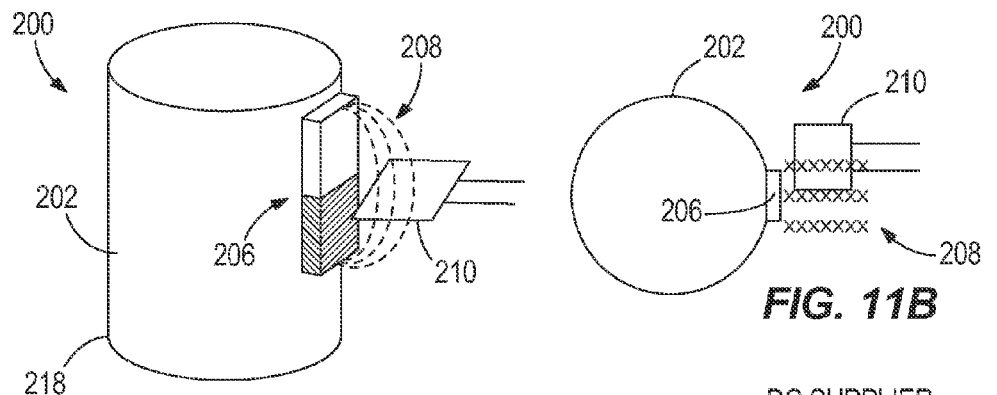
FIG. 11A
FIG. 11B
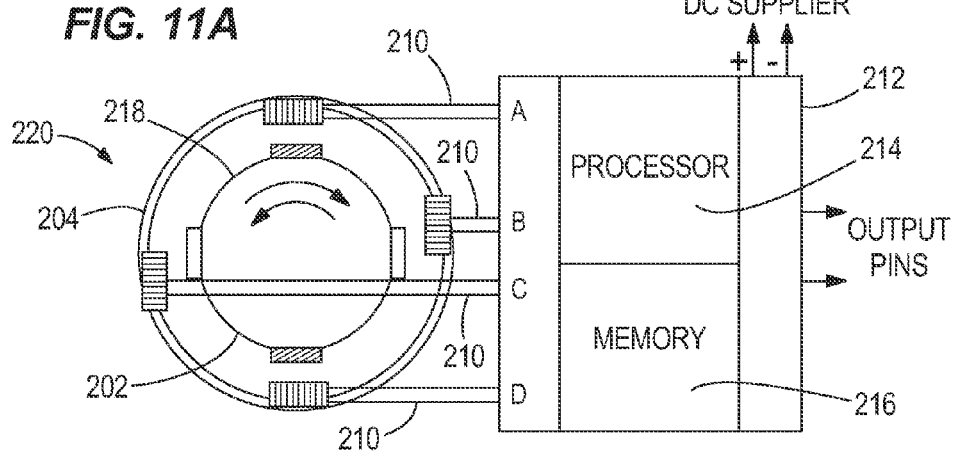
FIG. 11C
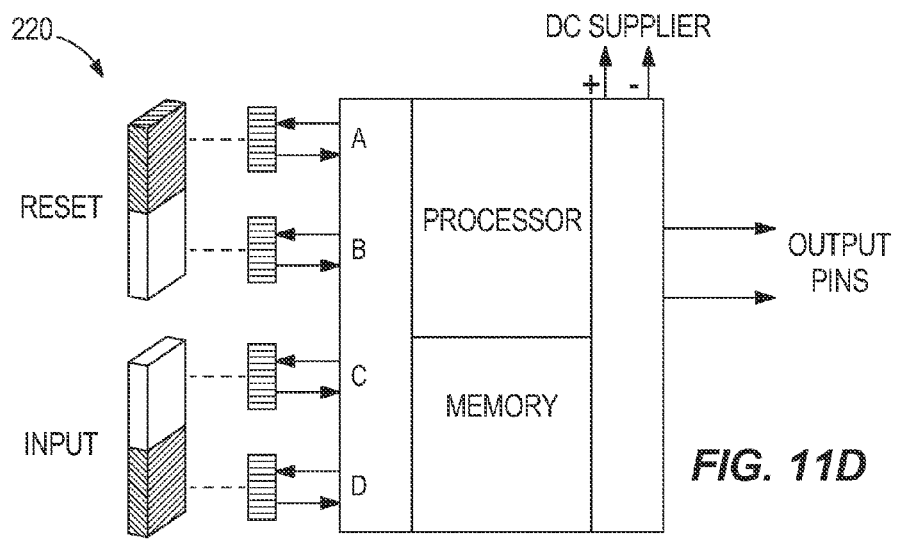
FIG. 11D

FILTERS, FILTER ASSEMBLIES, FILTER SYSTEMS AND METHODS FOR IDENTIFYING INSTALLATION OF QUALIFIED FILTER ELEMENTS

CROSS-REFERENCE TO RELATED APPLICATION

The present application is a divisional of U.S. patent application Ser. No. 13/864,964, filed Apr. 17, 2013, which claims the benefit of and priority to U.S. Provisional Patent Application Ser. No. 61/640,420, filed Apr. 30, 2012. Both applications are incorporated herein by reference in their entirety.

FIELD

The present disclosure relates to filters, and more particularly to filters, assemblies, systems and methods for identifying installation of qualified filter elements.

BACKGROUND

U.S. Pat. No. 6,533,926, which is incorporated herein by reference in entirety, discloses a replaceable filter cartridge that includes an end plate having a data component electrically coupled to a pair of concentric circuit rings. The data component may include a sensor, data chip, or resistor and is configured to provide filtration information to a remote station when the filter cartridge is positioned within the housing of a filtration assembly such that the circuit rings connect with electrical contacts in the housing.

U.S. Pat. No. 6,537,444, which is incorporated herein by reference in entirety, discloses a replaceable filter cartridge that includes a filter element and an end plate bonded to an end thereof. The end plate includes at least two electrical contacts and a key way that includes a relief section. Upon proper installation of the filter cartridge into the housing of a filter assembly, a key attached to a centerpost of the housing is received in the relief section of the end plate and the electrical contacts thereof make contact with corresponding electrical contacts in the housing causing a data component to be energized. The data component may include a sensor, data chip, or resistor assembled to an exposed surface of the endplate.

U.S. Pat. Nos. 7,615,151 and 7,850,845, which are incorporated herein by reference in entirety, disclose filters with installation integrity that permit fluid flow only in a first installation condition and not in a second undesired or mis-installation condition, including improper alignment or mounting of a filter element in a housing, an incorrect replacement filter element, absence of a filter element, and an incorrect housing cover. A magnetically actuated valve has a piston controlling fluid flow according to installation condition.

U.S. patent application Ser. No. 13/092,310, which is incorporated herein by reference in entirety, discloses a water sensor for a fuel filtration apparatus that includes a main body with at least one electrical contact disposed proximate the first end of the main body. The electrical contact(s) is operatively connectable to an electronic control unit. Multiple sensor contacts are disposed proximate a second end of the main body. The sensor contacts are configured to detect multiple water levels and provide an output on each water level detected. The electrical contact is configured to send the output to an electronic control unit. The water level information provided by the water sensor can be tracked by a control device to determine if the fill rate of water meets an alarm value.

U.S. Patent Application No. 61/355,401, which is incorporated herein by reference in entirety, discloses a run-safe filter system for confirming installation of a qualified filter element in a housing. An electrical switch has a first electrical condition in response to a qualified filter element being installed in the housing, and a second electrical condition in response to the absence of a qualified filter element installed in the housing.

SUMMARY

This Summary is provided to introduce a selection of concepts that are further described herein below in the Detailed Description. This Summary is not intended to identify key or essential features of the claimed subject matter, nor is it intended to be used as an aid in limiting the scope of the claimed subject matter.

In some examples, filter assemblies comprise a qualified filter element that filters fuel, a filter housing for the qualified filter element, and a water-in-fuel sensor that senses presence of water in the filter housing. The assemblies are configured such that an electrical resistance of the water-in-fuel sensor changes based upon whether the qualified filter element is installed in the housing.

In other examples, filter systems comprise a qualified filter element that filters fuel, a filter housing for the qualified filter element, a water-in-fuel sensor that senses presence of water in the filter housing, and a control circuit that determines whether there is water in the filter housing based upon an electrical resistance of the water-in-fuel sensor. The control circuit is electrically connected to the water-in-fuel sensor and determines whether the qualified filter element is installed in the housing based upon the electrical resistance of the water-in-fuel sensor.

In further examples, methods are for identifying a qualified filter element in a filter assembly having a filter housing. The methods comprise: providing a water-in-fuel sensor having an electrical circuit comprising a first portion located with the housing and a second portion located with the qualified filter element, inserting the qualified filter element into the filter housing, sensing with a control circuit a change in electrical resistance of the water-in-fuel sensor, and indicating that the qualified filter element is installed in the filter housing based on the change in electrical resistance.

In further examples, filter assemblies comprise a filter housing, a qualified filter element, and a plurality of magnetic elements on at least one of the filter housing and the qualified filter element. Each magnet in the plurality of magnetic elements has a magnetic field. A plurality of wires is disposed on at least the other of the filter housing and the qualified filter element. A control circuit is electrically coupled to the plurality of wires and detects an electrical current in the plurality of wires. When the qualified filter element is installed in the filter housing, the plurality of wires cuts the magnetic field of at least one of the plurality of magnetic elements and thereby changes the electrical current in the plurality of wires. The control circuit determines that the qualified filter element is installed in the filter housing based on a change in the electrical current in the plurality of wires.

In further examples, methods are for identifying a qualified filter element in a filter assembly having a filter housing. The methods comprise: providing a plurality of magnetic elements on at least one of the qualified filter element and the filter housing, the plurality of magnetic elements comprising a magnetic field; providing a plurality of wires on at least the other of the qualified filter element and the filter housing; installing the qualified filter element into the filter housing; sensing with a control circuit an electrical current along the plurality of wires; and identifying with the control circuit that the qualified filter element is installed in the filter housing when the electrical current across the wires changes.

BRIEF DESCRIPTION OF THE DRAWINGS

Examples of filters, assemblies, systems and methods for identifying installation of qualified filter elements in a filter housing are described with reference to the following figures. Like numbers are used throughout the figures to reference similar features and components.

FIGS. 7A-7D are examples of water-in-fuel sensors and end cap combinations.

FIGS. 8A-8B are further examples of water-in-fuel sensors and end cap combinations.

FIGS. 9A-9F are examples of locking arrangements for water-in-fuel sensors and end cap combinations.

FIGS. 11A-11D are examples of filter assemblies having a plurality of magnetic elements, a plurality of wires, and a control circuit that is electrically coupled to the wires and monitors a current in the wires.

DETAILED DESCRIPTION

In the present Detailed Description, certain terms have been used for brevity, clearness and understanding. No unnecessary limitations are to be inferred therefrom beyond the requirement of the prior art because such terms are used for descriptive purposes only and are intended to be broadly construed. The different filters, assemblies, systems and methods described herein may be used alone or in combination with other filters, assemblies, systems and methods. Various equivalents, alternatives, and modifications are possible within the scope of the appended claims.

Figure 1:
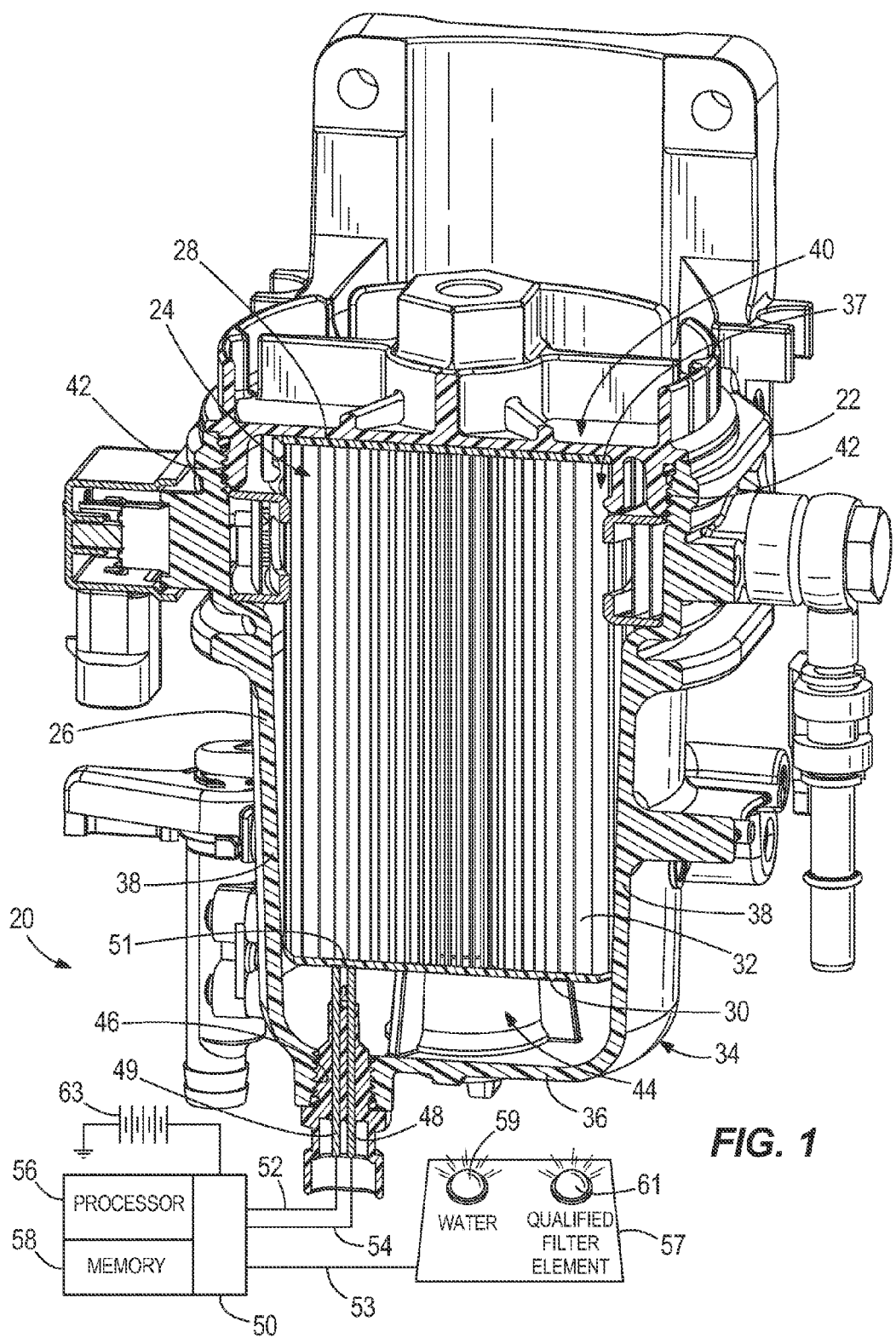
FIG. 1 depicts a filter system for filtering fuel.

FIG. 1 depicts a filter system 20 for filtering fuel. The filter system 20 includes a filter assembly 22 having a replaceable, qualified filter element 24 that is contained in a reusable filter housing 26. The shapes and configurations of the qualified filter element 24 and filter housing 26 are merely exemplary can widely vary from that which is shown and described. That is, the concepts of the present disclosure can be applied to a wide variety of filtration systems and assemblies. In the particular example shown, the qualified filter element 24 is a cylindrical cartridge that is installed into a correspondingly cylindrical reusable filter housing 26. The qualified filter element 24 has top and bottom end caps 28, 30 and a pleated filter media 32 is disposed therebetween. The filter housing 26 has a base receptacle 34 with a lower end wall 36 and upwardly extending circumferential sidewalls 38. The lower end wall 36 and upwardly extending circumferential sidewalk 38 together define a cavity 37 for receiving and housing the qualified filter element 24. A cover 40 is removably connectable to the top of the circumferential sidewalk 38 via a threaded connection 42. Attachment of the cover 40 closes the cavity 37 and secures the qualified filter element 24 in place. In this example, the base receptacle 34 also has a centerpost 44 that extends into an inner circumferential aperture 43 in the qualified filter element 24. In some examples, an upper end (not shown) of the centerpost 44 can connect to or abut a lower surface (not shown) of the top end cap 28, as is conventional. As is conventional, fuel that flows through the filter assembly 22 flows through the filter media 32 for filtering impurities therefrom.

Figure 2:
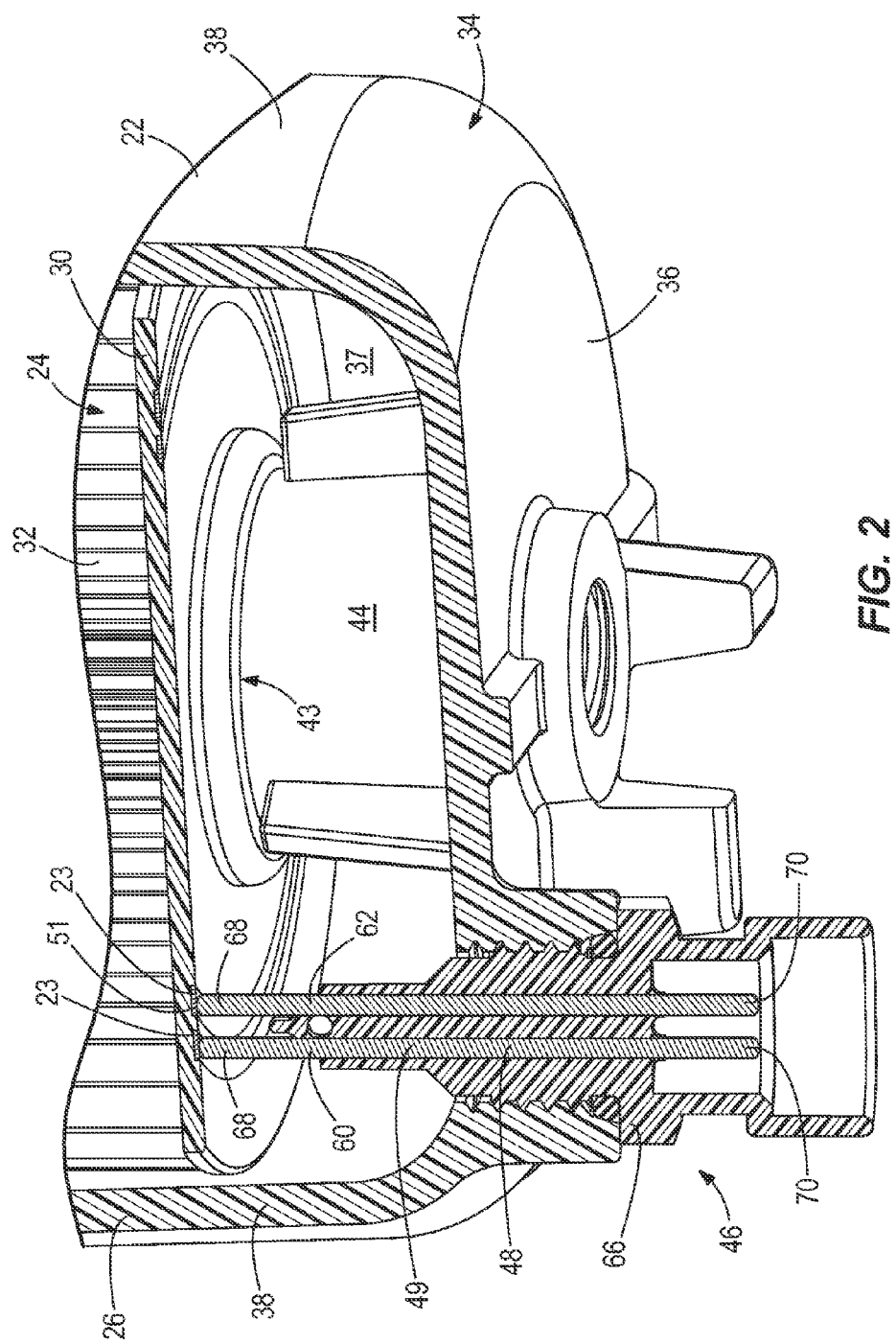
FIG. 2 is a partial view of a filter assembly shown FIG. 1, showing a water-in-fuel sensor.

Referring to FIGS. 1 and 2, the filter assembly 22 also includes a unique water-in-fuel (hereinafter "WIF") sensor 46 that is configured to sense a presence of water in the filter housing 26. Water that occurs in fuel filter housings can adversely affect performance of the filter assembly and therefore it is desired to diagnose a water condition in fuel filter housings as soon as it occurs. In this example, the WIF sensor 46 is configured to advantageously detect when a certain level of water accumulates at the bottom of the base receptacle 34 so that an operator can be alerted to the situation and take corrective action. The basic functionality of a WIF sensor is well known by those having ordinary skill in the art. Examples of conventional WIF sensors are provided in the applicant's U.S. Patent Application Publication No. 2011/0259802, which is incorporated herein by reference. WIF sensors operate based upon the principle that fuel has a very low conductivity, and for all practical purposes, can be considered an electrical insulator. Water, on the other hand, is relatively conductive due to the impurities in the water. Conventional WIF sensors have an electrical circuit (hereinafter a "WIF circuit") that receives an electrical current. The WIF circuit provides a resistance to the electrical current. The amount of resistance will vary depending upon whether a portion of the sensor is disposed in water or fuel. Based on these principles, WIF sensors allow an operator can readily diagnose whether there is water in the fuel by monitoring the level of resistance in, the sensor.

The unique WIF sensor 46 shown in FIGS. 1 and 2 differs from conventional WIF sensors in that it includes an electrical circuit (hereinafter "WIF circuit") 48 having a first portion 49 that is located with the filter housing 26 and a second portion 51 that is located with the qualified filter element 24. The discrete first and second portions 49, 51 are oriented such that proper installation of the qualified filter element 24 in the filter housing 26 electrically connects the first and second portions 49, 51 and thereby provides a more complete WIF circuit 48 of the WIF sensor 46 and modifies the electrical resistance of the first portion 49. As will be explained further herein below, separating the WIF sensor 46 into discrete portions that respectively are disposed on the qualified filter element 24 and on the filter housing 26 provides improved filter systems 20, filter assemblies 22 and methods of use that readily allow an operator to identify whether or not a filter element that is installed into the filter housing 26 is a qualified filter element 24, as opposed to a counterfeit or any other non-conforming filter element. Installation of a qualified filter element 24 actively, electrically connects the first and second portions, 49, 51, thereby changing the resistance of the WIF circuit 48, and thereby indicating that the qualified filter element 24 has been installed. The exact nature and configuration of the noted first and second portions 49, 51 can vary from that which is shown in FIGS. 1 and 2, as is evident from the examples discussed herein below with reference to the remaining Figures. Also the WIF sensor 46 does not need to be located at the bottom of the base receptacle 34 and depending upon the orientation of the filter housing 26 and fluid flow therethrough, the WIF sensor 46 can instead be located to diagnose water conditions at other locations in the filter housing 26.

In the particular example shown in FIGS. 1 and 2, the first portion 49 of the WIF circuit 48 includes first and second electrical contacts, which in this example are elongated metal pins 60, 62 that extend through a body 66 of the WIF sensor 46. Other amounts and types of electrical contacts can also or instead be employed, and can also include plug holes and/or the like. In this example, the WIF sensor 46 is installed in the lower end wall 36 and both of the first and second pins 60, 62 have first ends 68 that extend into the base receptacle 34 and second ends 70 that extend out of the base receptacle 34. The first ends 68 are for sensing whether there is water in the filter housing 26 and the second ends 70 are for connecting to a control circuit 50, as will be described further herein below. The second portion 51 of the WIF circuit 48 is located with the qualified filter element 24 and includes conductive material 23 that electrically connects the first ends 68 of the pins 60, 62 together when the qualified filter element 24 is properly installed in the filter housing 26. In this example, the conductive material 23 is located on the bottom end cap 30 of the qualified filter element 24; however the conductive material 23 does not have to be located at the bottom end cap 30 and instead could be located elsewhere on the qualified filter element 24 in any location where conductive material 23 effectively electrically connects the first ends 68 of the first and second pins 60, 62 when the qualified filter element 24 is installed in the housing. In this example, the conductive material 23 includes any conductive metal; however the nature and configuration of the conductive material 23 can widely vary and different configurations of the conductive material 23 are further described herein below with reference to FIGS. 5-8.

Referring to FIG. 1, the filter system 20 also includes a control circuit 50 that is electrically connected to the WIF sensor 46 by electrical links 52, 54 extending between the control circuit 50 and the second ends 70 of the first and second pins 60, 62. The control circuit 50 includes a programmable processor 56 and a memory 58. As is conventional, the programmable processor 56 can be communicatively connected to a computer readable medium that includes volatile or nonvolatile memory upon which computer readable medium is stored. The programmable processor 56 can access the computer readable medium and upon executing the computer readable code carries out the functions as described herein. The control circuit 50 can be any suitable control device for interpreting information detected by the WIF sensor 46 and can be, but is not limited to an engine control module (ECM), a controller, a fluid management control module, or any suitable data/information processing device, which may employ one or more software routines, as appropriate. In this example, the control circuit 50 is powered by any conventional power source, such as for example one or more batteries 63. Through the electrical links 52, 54, the control circuit 50 is configured to supply an electrical current to one of the first and second pins 60, 62 extending through the WIF sensor 46 and to receive electrical current from the other of the first and second pins 60, 62. However the control circuit 50 does not have to supply electrical current to the pins 60, 62; rather the noted electrical current could be directly provided to the WIF sensor 46 by any other power source such a battery. Through the electrical links 52, 54, the control circuit 50 is electrically connected to the WIF sensor 46 such that changes in electrical resistances of the WIF sensor 46 are sensed by the control circuit 50. As described further herein below, based upon such changes of electrical resistance, the control circuit 50 is programmed to identify both whether there is water in the noted fuel and also whether there is a qualified filter element 24 installed in the filter housing 26.

The filter system 20 optionally can include an output device 57 having warning lights 59, 61 and/or other conventional means for alerting an operator as to whether there is water in the filter housing 26 and whether there is a qualified filter element 24 installed in the filter housing 26. The control circuit 50 is electrically connected to the output device 57 via a wired or wireless communication link 53 across which electronic signals can be sent by the control circuit 50 and received by the output device 57. The control circuit 50 is programmed to control output device 57 to light the warning lights 59, 61 when the control circuit 50 determines that there is water in the filter housing 26 and when the control circuit 50 determines that there is a qualified filter element 24 in the filter housing, respectively. The type of output device 57 can vary from that shown and described, and can for example include any conventional output means for communicating information to an operator, such as video screens, LED light displays, audio speakers, and/or the like.

Figure 3:
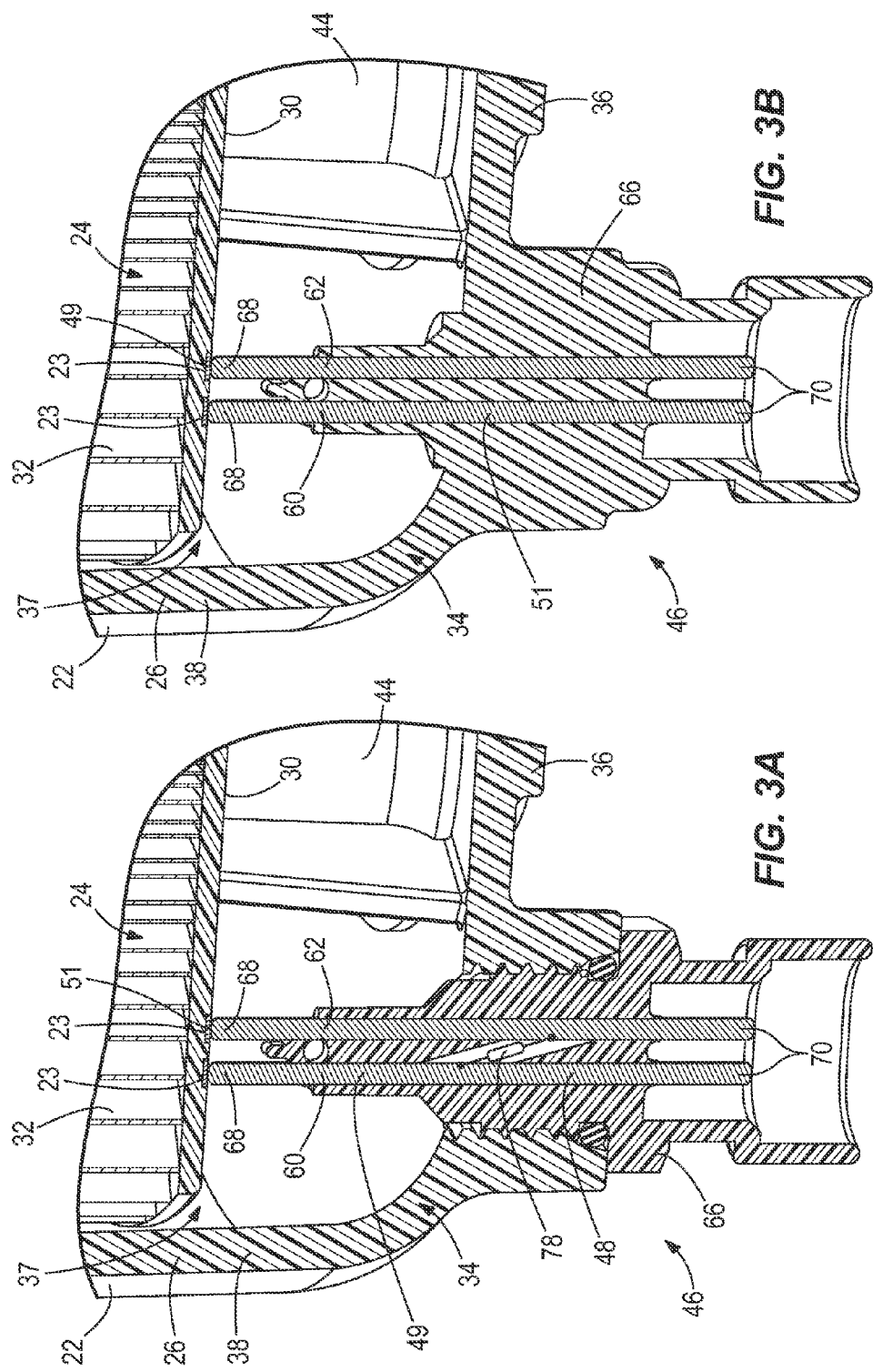
FIG. 3A is another example of a water-in-fuel sensor for the filter assembly.
FIG. 3B is another example of a water-in-fuel sensor for the filter assembly.

In the example shown in FIGS. 1 and 2, the body 66 of the WIF sensor 46 is connected to the lower end wall 36 via a threaded connection 64. Thus the WIF sensor 46 is installed by rotating one of the WIF sensor 46 and filter housing 26 with respect to the other. However the threaded connection 64 is just one of many examples of possible permanent or temporary connections between the WIF sensor 46 and the lower end wall 36. In another example shown in FIG. 3B, the body 66 of the WIF sensor 46 can be permanently molded as a part of the lower end wall 36, such that the WIF sensor 46 is part of the filter housing 26. While the type of connection of the WIF sensor 46 to the filter housing 26 is not critical and can vary from that shown and described, the type of connection does impact the manner in which the conductive material 23 of the second portion 51 and pins 60, 62 of the first portion 49 are effectively aligned when the qualified filter element 24 is installed in the filter housing 26. This will be discussed further herein below with reference to FIGS. 9A-9F.

Referring to FIGS. 1 and 2, in use, when there is no water present in the filter housing 26 and when the qualified filter element 24 is not installed in the filter housing 26, an open circuit across the pins 60, 62 will be detected by the control circuit 50. That is, electrical current that is applied to the WIF circuit 48 will not completely flow through pins 60, 62 and back to the control circuit 50 because the pins 60, 62 are not electrically connected to each other. When such an open circuit is detected, the control circuit 50 is programmed to control the output device 57 to indicate that there is no water in the filter housing 26 and that the qualified filter element 24 is not installed in the filter housing 26. If there is water inside the filter housing 26 that rises to a level such that both ends 68 of first and second pins 60, 62 are submerged in the water, a relatively low resistance across the pins 60, 62 will be detected by the control circuit 50 because of the relatively high conductivity of the water. That is, the water electrically connects the ends 68 of the first and second pins 60, 62 and it also provides a low level of resistance to current flow. The control circuit 50 is programmed to monitor the total resistance across the pins 60, 62 and to compare this resistance with one or more resistance values stored in the memory 58. The resistance values can for example be stored in the memory in the form of a lookup table or other list that corresponds known resistance values to conditions of the WIF sensor 46. The memory 58 has a stored resistance value that corresponds to a situation where the ends 68 of the pins 60, 62 are submerged in water. When a resistance in the WIF circuit 48 is identified by the control circuit 50 that corresponds to this stored resistance value, the control circuit 50 is programmed to communicate with and control the output device 57 via the communication link 53 to indicate that there is water in the filter housing 26.

Similarly, the resistance of the WIF sensor 46 will also change when the qualified filter element 24 is installed in the filter housing 26 such that the ends 68 of the first and second pins 60, 62 are connected by the conductive material 23. Electric current from the control circuit 50 will flow across the first and second pins 60, 62 via the conductive material 23. The conductive material 23 will provide a certain resistance to the flow of current across the pins 60, 62. The control circuit 50 is programmed to monitor the resistance across the pins 60, 62 and to compare this resistance with one or more resistance values stored in the memory 58. In one example, when the control circuit 50 identifies any current flow across the pins 60, 62 whatsoever, the control circuit 50 is programmed to control the output device 57 to indicate that the qualified filter element 24 is installed in the filter housing 26 or that there is water in the filter housing 26. In another example, the memory 58 has a stored resistance value in a lookup table or other list that corresponds to the condition where the qualified filter element 24 is installed in the filter housing 26. When a resistance in the WIF sensor 48 is identified by the control circuit 50 that corresponds to this stored resistance value, the control circuit 50 is programmed to control the output device 57 to indicate that the qualified filter element 24 is installed in the filter housing 26.

As discussed herein above, the configuration of the WIF circuit 48 can vary. FIG. 3A depicts another example wherein the WIF sensor 46 includes a resistor 78 that extends between and electrically connects the first and second pins 60, 62. Similar to the example in FIG. 2, the control circuit 50 applies an electrical current to the noted first and second pins 60, 62, which are connected by the resistor 78. If the qualified filter element 24 is not installed in the filter housing 26 and there is no water in the filter housing 26, the electrical current will encounter a known or predictable resistance provided by the resistor 78. The control circuit 50 is programmed to monitor the resistance across the pins 60, 62 and to compare the monitored resistance with one or more resistance values stored in the memory 58. The memory 58 has a stored resistance value that corresponds to the situation where the qualified filter element 24 is not installed in the filter housing 26 and there is no water in the filter housing 26 and the known resistance is provided by the resistor 78. When a resistance in the WIF sensor 48 is identified by the control circuit 50 that corresponds to this stored resistance value, the control circuit 50 is programmed to control the output device 57 to indicate that the qualified filter element 24 is not installed in the filter housing 26 and there is no water in the filter housing 26.

When the filter element 24 is not installed in the filter housing 26 and there is water in the filter housing 26 that electrically connects the ends 68 of the first and second pins 60, 62, some electrical current will flow across the ends 68 of the pins 60, 62 because water will typically provide less resistance to the current than the resistance provided by the resistor 78. In some examples, some of the electrical current still could also flow across the resistor 78. The relative amounts of current flow across the pins 60, 62 and the resistor 78 will depend upon the resistance provided by each. The control circuit 50 is programmed to monitor the total resistance across the pins 60, 62 and to compare this resistance with one or more resistance values stored in the memory 58. The memory 58 has a stored resistance value that corresponds to the situation where the pins 60, 62 are submerged in water. When a resistance in the WIF sensor 48 is identified by the control circuit 50 that corresponds to this stored resistance value, the control circuit 50 is programmed to control the output device 57 to indicate that there is water in the filter housing 26.

When the qualified filter element 24 is installed in the filter housing 26, the ends 68 of the first and second pins 60, 62 are connected by the conductive material 23, and the conductive material 23 will provide a certain resistance to the flow of current across the pins 60, 62, which typically will be less than the resistance provided by resistor 78. The relative amounts of current flow across the pins 60, 62 and the resistor 78 will depend upon the resistance provided by each. Again, the control circuit 50 is programmed to monitor the resistance across the pins 60, 62 and to compare this resistance with one or more resistance values stored in the memory 58. The memory 58 has a stored resistance value that corresponds to the situation where the qualified filter element 24 is installed in the filter housing 26 and current flows across the conductive material 23, and optionally also the resistor 78. When a resistance in the WIF sensor 48 is identified by the control circuit 50 that corresponds to this stored resistance value, the control circuit 50 is programmed to control the output device 57 to indicate that the qualified filter element 24 is installed in the filter housing 26.

Figure 4:
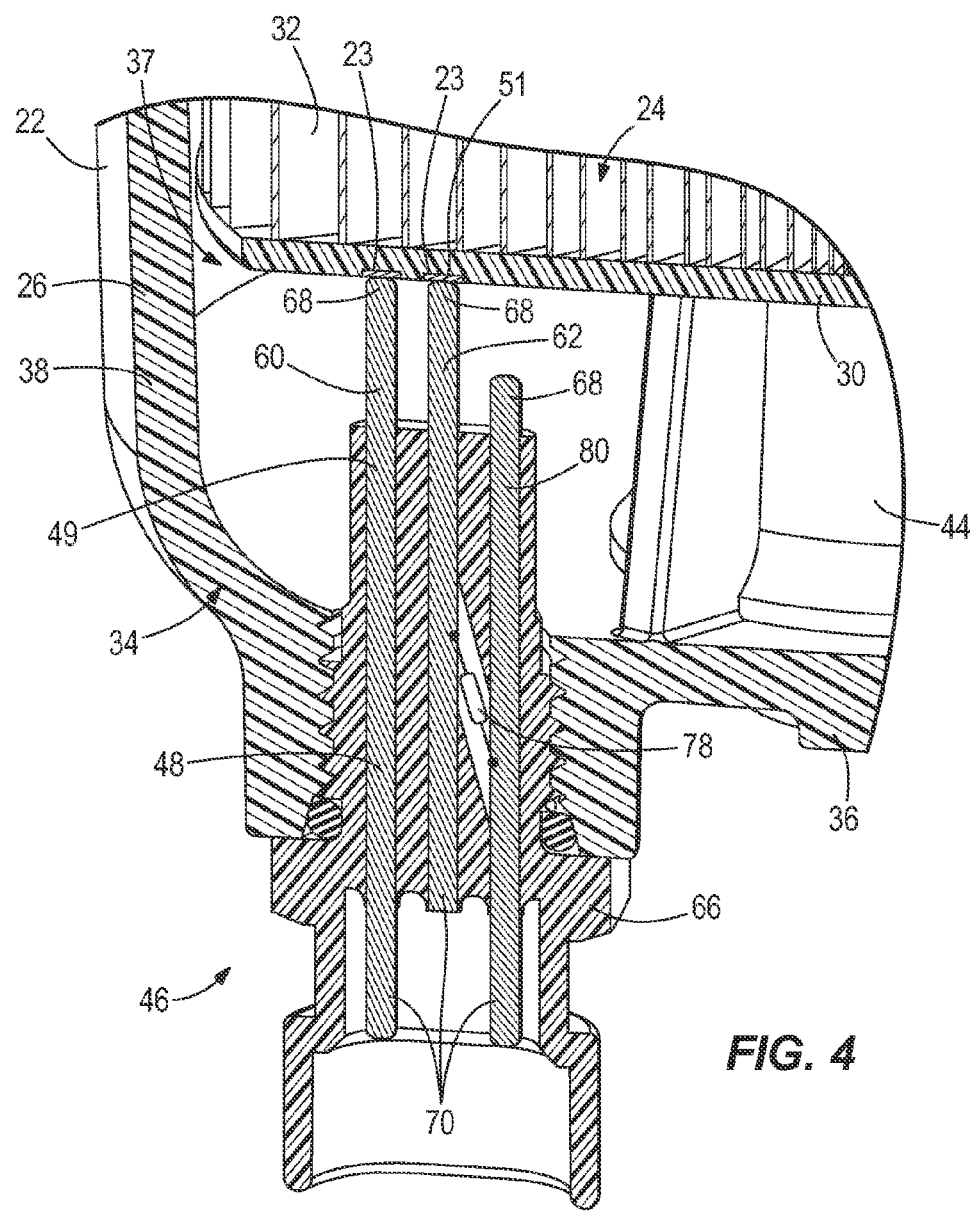
FIG. 4 is another example of a water-in-fuel sensor for the filter assembly.

FIG. 4 depicts another example of a WIF sensor 46. In this example, the first portion 49 of the WIF circuit 48 has three pins 60, 62, 80. Pins 60 and 62 have ends 68 that extend into the filter housing 26. Pins 60 and 80 have ends 70 that extend out of the filter housing 26. The pins 62 and 80 are connected by a resistor 78. When a qualified filter element 24 is not installed and the pins 60, 62 are not in water, no current will flow through the WIF sensor 46. The control circuit 50 will sense an open circuit and will control the output device 57 to indicate this condition, as discussed in the example of FIGS. 1 and 2. When a qualified filter element 24 is installed in the filter housing 26, the conductive material 23 on the bottom end cap 30 electrically connects the ends 68 of the pins 60, 62, thus connecting the first and second portions 49, 51 of the noted WIF circuit 48. Electrical current will flow across the ends 68 of the pins 60, 62 via the conductive material 23 and across the resistor 78 connecting the pins 62, 80. The total resistance provided by the conductive material 23 and the resistor 78 will be detected by the control circuit 50. The control circuit 50 is programmed to monitor the resistance across the pins 60, 62, 80 and to compare this resistance with one or more resistance values stored in the memory 58. The memory 58 has a stored resistance value that corresponds to the situation where the qualified filter element 24 is installed in the filter housing 26. When a resistance in the WE circuit 48 is identified by the control circuit 50 that corresponds to this stored resistance value, the control circuit 50 is programmed to control the output device 57 to indicate that the qualified filter element 24 is installed in the filter housing 26.

Also, once there is water inside the filter housing 26 that rises to a level such that the first and second pins 60, 62 are submerged in the water, a relatively low resistance across the pins 60, 62 will be detected by the control circuit 50 because of the relatively high conductivity of the water. That is, the water electrically connects the ends 68 of the first and second pins 60, 62 and also provides some resistance to current flow through the pins 60, 62; however this resistance will typically be less than the resistance provided by the conductive material 23 and the resistor 78. The control circuit 50 is programmed to monitor the resistance across the pins 60, 62 and to compare this resistance with one or more resistance values stored in the memory 58. The memory 58 has a stored resistance value that corresponds to the situation where the pins 60, 62 are submerged in water. When a resistance in the WIF circuit 48 is identified by the control circuit 50 that corresponds to this stored resistance value, the control circuit 50 is programmed to control the output device 57 to indicate that there is water in the filter housing 26.

As discussed herein above, the construction and orientation of the second portion 51 of the WIF circuit 48 can vary. In one example, with reference to FIG. 5A, the conductive material 23 forms a pair of concentric conductive rings 72, 74 that are circumferentially disposed around the bottom end cap 30. The concentric conductive rings 72, 74 are connected together by a radially extending conductive junction 76. The concentric conductive rings 72, 74 and the pins 60, 62 of the WV sensor 46 are both oriented and equally spaced apart such that when the qualified filter element 24 is properly installed in the filter housing 26, the concentric conductive rings 72, 74 are aligned with and engage with the ends 68 of the contacts or pins 60, 62, to thereby join the first and second portions 49, 51 and complete the WIF circuit 48. This configuration for the second portion 51 alternatively can be applied in combination with any of the configurations for the first portion 49 shown in FIGS. 1-4. Also, the conductive material 23 does not have to be formed into a concentric ring shape and does not have to be circumferentially aligned around the bottom end cap 30, as will be apparent from other examples in the following drawing figures.

Figure 5A:
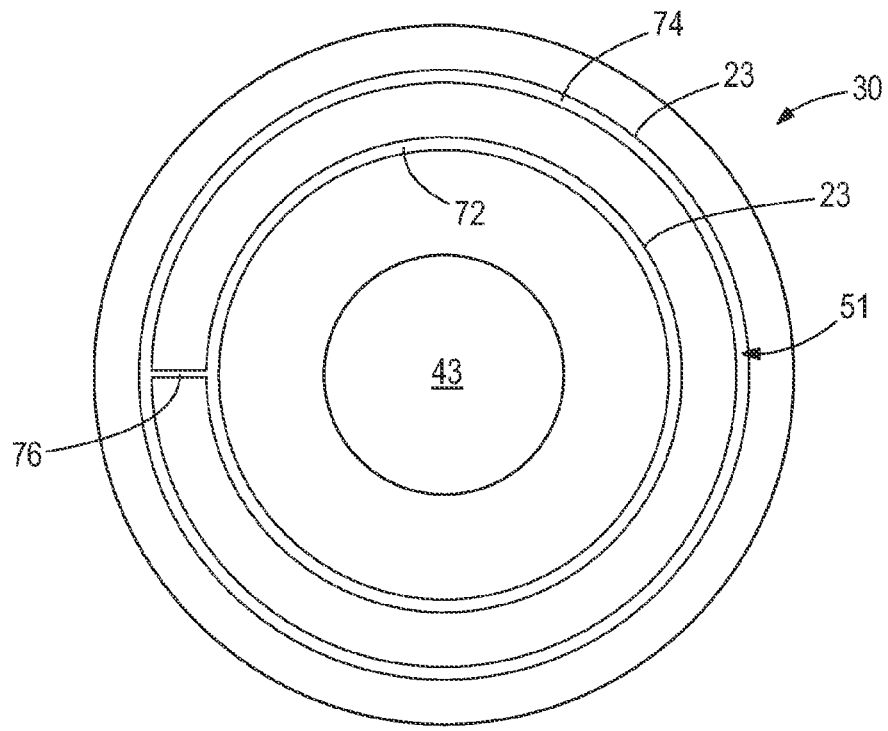
FIGS. 5A-5B are examples of an end cap on a filter housing of the assembly.
Figure 5B:
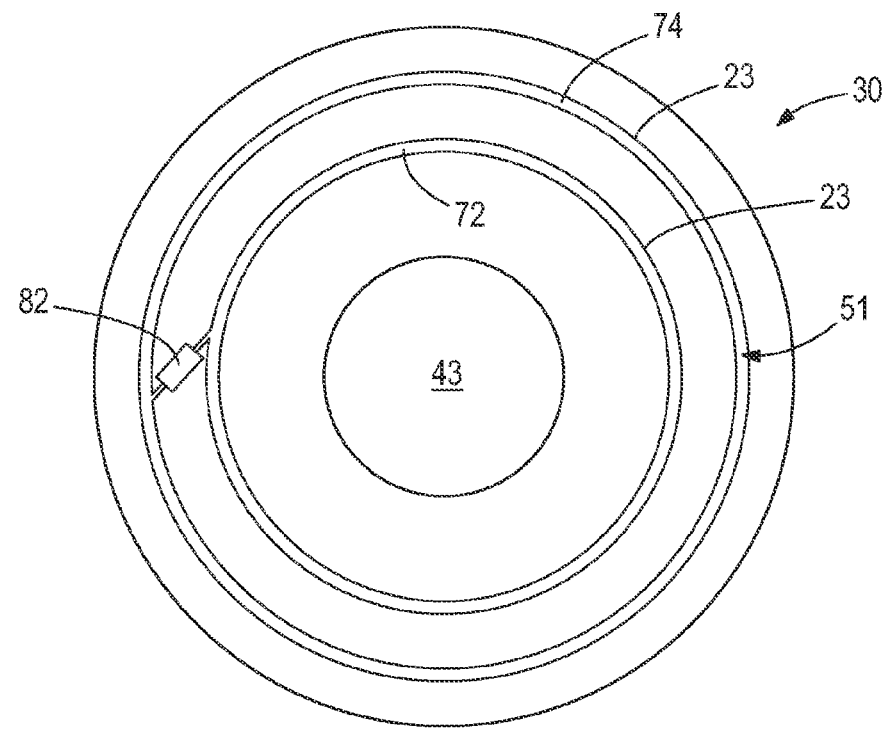

The example shown in FIG. 5B is like the example of FIG. 5A, except that it includes a resistor 82 instead of the radially extending conductive junction 76. Resistor 82 is located with the second portion 51 and electrically connecting to the concentric conductive rings 72, 74. This configuration for the second portion 51 alternately can be applied in combination with any of the configurations shown in FIGS. 1-4. When the configuration of FIG. 5B is used in combination with the configurations of FIG. 3A and FIG. 4, the WIF circuit 48 will include two resistors 78, 82 that are electrically connected in parallel when qualified filter element 24 is installed and the first portion and second portion 49, 51 are joined together. Resistor 78 is located with the first portion 49 and resistor 82 is located with the second portion 51.

Figure 6A:
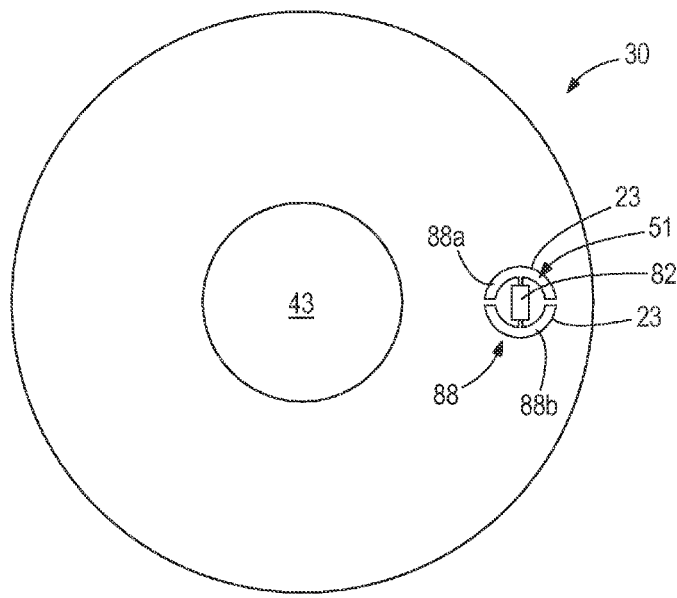
FIGS. 6A-6B are further examples of an end cap on a filter housing of the assembly.

FIG. 6A depicts another example of the second portion 49 on bottom end cap 30, wherein the conductive material 23 includes a bifurcated non-circumferential conductive ring 88 for connecting the ends 68 of the first and second pins 60, 62 when the qualified filter element 24 is installed in the filter housing 26. The diameter of the non-circumferential conductive ring 88 is substantially the same as the distance between the first and second pins 60, 62 to assist the noted connection. A resistor 82 is located with the second portion and electrically connects two halves 88a, 88b of the non-circumferential ring 88. This configuration for the second portion 51 alternately can be applied in combination with any of the configurations shown in FIGS. 1-4. When the configuration of FIG. 6A is used in combination with either of the configurations of FIG. 3A or FIG. 4, the WIF circuit 48 will include two resistors 78, 82 in series when qualified filter element 24 is installed and the first portion and second portion 49, 51 are joined together. Resistor 78 is located with the first portion 49 and resistor 82 is located with the second portion 51.

Figure 6B:
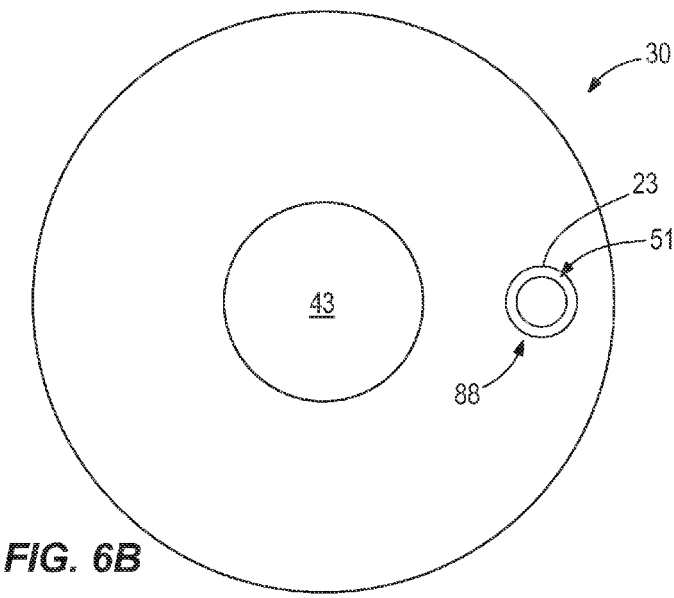

FIG. 6B is an example like FIG. 6A, except the circumferential conductive ring 88 is a complete circle that is molded into the bottom end cap 30 and thus does not require the noted resistor 82 or another type of junction.

FIGS. 7A-7D depict some of the many potential combinations and configurations of the noted first and second portions 49, 51 of the WIF circuit 48. In FIG. 7A, the bottom end cap 30 is entirely (or at least partly) formed of conductive material 23 such that the bottom end cap 30 itself forms the noted second portion 51 for completing the WIF circuit 48. Installation of the qualified filter element 24 in the filter housing 26 causes the ends 68 of the first and second pins 60, 62 to contact the bottom end cap 30, thus completing the noted WIF circuit 48. This configuration for the second portion 51 can be applied in combination with any of the configurations shown in FIGS. 1-4.

FIG. 7B depicts a combination of the WIF sensor 46 and end cap 30 shown in FIGS. 3A and 5B, respectively, as described herein above.

FIG. 7C, depicts a combination of the WIF sensor 46 and end cap 30 shown in FIGS. 2 and 5B, respectively, as described herein above.

FIG. 7D depicts a combination of the WIF sensor 46 and end cap 30 shown in FIGS. 4 and 5A, respectively, as described herein above.

FIGS. 8A and 8B depict examples wherein the first and second portions of the WIF circuit 48 are connected together by an intermediate conductive element 90 when the qualified filter element 24 is installed in the filter housing 26. These examples illustrate that the first and second portions 49, 51 do not have to be directly connected together, but instead can be connected by an intermediate conductive device. In FIG. 8A, the conductive element 90 includes part of the filter housing 26, and particularly a conductive metal casing 92 that connects the first pin 60 to the bottom end cap 30. In this example, the bottom end cap 30 can be like the example in FIG. 7A, wherein all of or at least part of the bottom end cap 30 is formed of conductive material 23 and itself provides the second portion 51 of the WIF circuit 48. The conductive metal casing 92 is on an interior surface 94 of the filter housing 26 and is connected to the pin 60. The conductive casing 92 lines the interior of the base receptacle 34 and extends upwardly therein. At least the top end 115 of the conductive metal casing 92 engages with the conductive material 23 on the end cap 30 when the qualified filter element 24 is installed in the filter housing 26. The end 68 of the pin 62 also connects to conductive material 23, thus connecting the first and second portions 49, 51 of the WIF circuit 48, which functions like the example shown in FIG. 4.

In FIG. 8B the conductive element 90 includes a conductive metal casing 96 on the centerpost 44 of the filter housing 26. The conductive metal casing 96 connects the second and third pins 62, 80 to the conductive material 23 on the bottom end cap 30 when the qualified filter element 24 is properly installed in the filter housing 26. This completes the WIF circuit 48, which functions like the example shown in FIG. 4.

Through research and experimentation, the present inventors have also found that it is desirable that the radial orientation of the noted first and second portions 49, 51 of the WIF circuit 48 are automatically or easily aligned during installation such that the noted electrical connection is made between the first and second portions 49, 51 when the qualified filter element 24 is inserted in the filter housing 26. Thus, in the illustrated examples, it is desirable that the ends 68 of the first and second pins 60, 62 become aligned with the conductive element 23 of the qualified filter element 24 once the qualified filter element 24 is properly installed. FIGS. 9A-9F depict some of the combinations that can achieve this objective.

In FIG. 9A, the WIF sensor 46 is either locked to or formed as a part of the filter housing 26, such that the WIF sensor 46 cannot be rotated with respect to the filter housing 26. One example of this type of WIF sensor 46 is shown in FIG. 3B. The bottom end cap 30 is like the example shown in FIG. 7A, wherein a portion of or the entire bottom end cap 30 is made of conductive material 23 and thus itself provides the second portion 51 of the WIF circuit 48. In addition, the bottom end cap 30 is provided with radially concentric, circumferential grooves 84, 86 for receiving and engaging with the ends 68, 70 of the first and second pins 60, 62. The circumferential grooves 84, 86 are electrically connected by a radial junction groove 85. The bottom end cap 30 can be set at any rotational position with respect to the WIF sensor 46, because the entire circumference of the grooves 84, 86 consistently allows for electrical contact between the noted first and second portions 49, 51.

In FIG. 9B, the bottom end cap 30 is like the example shown in FIG. 7A, wherein a portion of or the entire bottom end cap 30 is made of conductive material 23 and thus itself provides the second portion 51 of the WIF circuit 48. In addition, the bottom end cap 30 is provided with a non-circumferential, circular conductive groove 93. A mechanical lock 99 is provided to retain the bottom end cap 30 such that the non-circumferential conductive groove 93 remains at a fixed circumferential position with respect to the WE sensor 46. The type of mechanical lock can widely vary, some examples are disclosed with respect to FIGS. 10A and 10B, described herein below. The body 66 of the WIF sensor 46 is connected to the filter housing 26 by the threaded connection 42, such that the body 66 is radially rotatable with respect to the filter housing 26. The circular shape and the fixed circumferential position of the conductive groove 93 ensures proper electrical connection between the ends 68 of the first and second pins 60, 62 regardless of the radial orientation of the body 66 of the WIF sensor 46 with respect to the filter housing 26. The mechanical lock 99 ensures that the conductive groove 93 is aligned with the ends 68 of the first and second pins 60, 62.

In FIG. 9C, the bottom end cap 30 is like the example shown in FIG. 7A wherein at least a portion of the bottom end cap 30 is made of conductive material 23 and thus itself provides the second portion 51 of the WIF circuit 48. In addition, the bottom end cap 30 is provided with the non-circumferential, circular conductive groove 93 formed therein. The WE sensor 46 is like the example shown in FIG. 3B, wherein the body 66 of the WIF sensor 46 is locked with or formed into the filter housing 26. The mechanical lock 99 locks the rotational orientation of the bottom end cap 30 with respect to the filter housing 26.

FIG. 9D depicts another example, wherein the bottom end cap 30 is like the example shown in FIG. 5A and the WIF sensor 46 is like the example shown in FIG. 3B. The body 66 of the WIF sensor 46 is locked with or a part of the filter housing 26. The concentric circumferential nature of the conductive rings 72, 74 ensure that connection between the first and second portions 49, 51 of the WIF circuit 48 occurs when the qualified filter element 24 is installed in the filter housing 26, regardless of the rotational position of the qualified filter element 24 with respect to the fixed WIF sensor 46.

FIG. 9E is like FIG. 9D except instead of the circumferential concentric conductive rings 72, 74, the bottom end cap 30 is provided with the circular, non-circumferential conductive ring 88. The mechanical lock 99 locks the rotational orientation of the bottom end cap 30 with respect to the filter housing 26. The body 66 of the WIF sensor 46 is locked with or a part of the filter housing 26. Thus the circumferential orientation of the non-circumferential conductive rings 87, 88 is aligned with the circumferential orientation of the WIF sensor 46 when the qualified filter element 24 is installed in the filter housing 26.

FIG. 9F depicts another example wherein the bottom end cap 30 is like the example in FIG. 7A and the first portion 49 of the WIF circuit 48 is like the example in FIG. 2. At least part of the bottom end cap 30 is made of conductive material 23 such that the circumferential alignment of the respective first and second portions 49, 51 is accomplished when the qualified filter element 24 is installed in the filter housing 26.

Figure 10B:
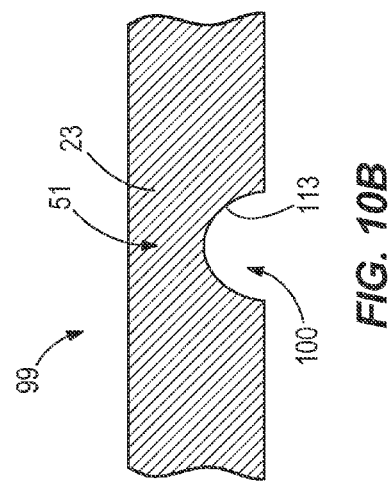
FIGS. 10A-10B are examples of mechanical locks for locking first or second portions of the electrical circuit with respect to each other.
Figure 10A:
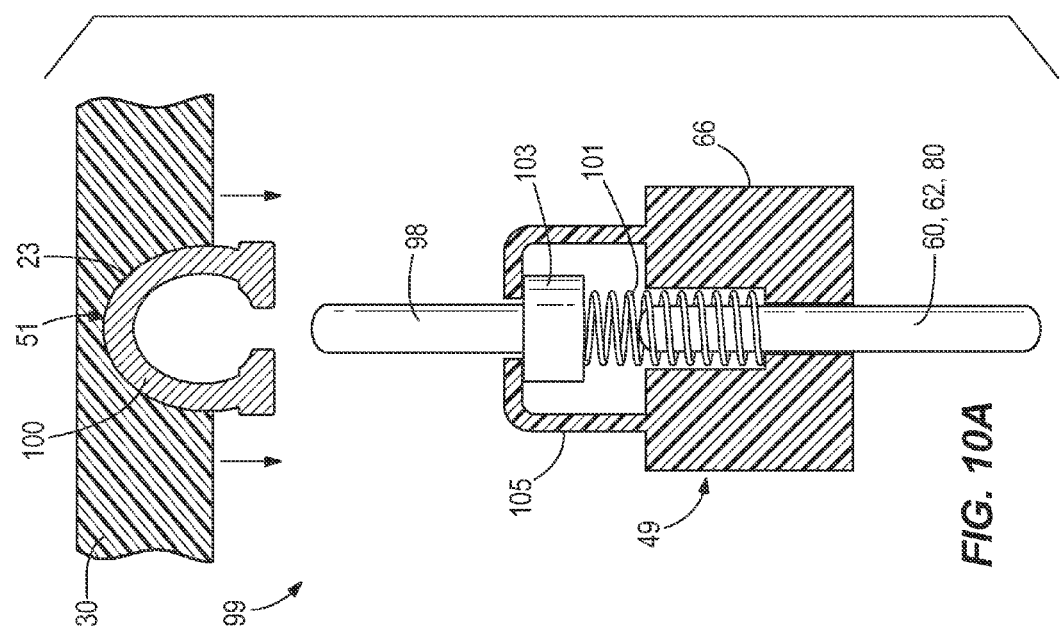

FIGS. 10A and 10B show some examples of mechanical locks 99 for locking the first and second portions 49, 51 of the WIF circuit 48 together. FIG. 10A depicts an example wherein a pin 98 is biased by a spring 101 to engage with a corresponding concave conductive ring 100 on the bottom end cap 30. The spring 101 is disposed on one of the pins 60, 62, 80 of the WIF sensor 46. The pin 98 has a head that 103 that engages the spring 101. The base of a bracket 105 engages the opposite side of the spring 101. Insertion of the qualified filter element 24 into the filter housing 26 moves the bottom end cap 30 towards the pins 60, 62 and optionally 80 of the WIF sensor 46, thus causing the concave conductive ring 100 to engage with the head 105 of pin 98. This compresses the spring 101 until the pin 98 contacts the pin 60, 62, 80, thus forming an electrical connection and completing the WIF circuit 48. FIG. 10B depicts an example of an end cap 30 for use with the assembly of FIG. 10A, wherein the concave conductive ring 100 is in the form of a conductive groove 113 formed in the bottom end cap 30.

FIGS. 11A-11B depict another example of a filter assembly 200 having a qualified filter element 202 and a filter housing 204 for the qualified filter element 202. At least one magnetic element 206 is disposed on the qualified filter element 202. The magnetic element 206 has a magnetic field 208 and can be a magnet or any other type of magnetic element. A pair of wires 210 are disposed on the filter housing 204. A control circuit 212 having a programmable processor 214 and memory 216 is electrically coupled to the wires 210 so as to monitor a current across the wires 210. In this example, the qualified filter element 202 is a cylindrical filter element having a circumferential outer surface 218. The magnetic element 206 is on the circumferential outer surface 218. The qualified filter element 202 can be installed in the filter housing 204 by rotating the qualified filter element 202 clockwise so that the magnetic element 206 passes by the plurality of wires 210 during the rotations. The qualified filter element 202 can be uninstalled in the filter housing 204 by rotating the qualified filter element 202 counterclockwise so that the magnetic element 206 passes by the plurality of wires 210 during the rotations.

Like the example in FIG. 1, the programmable processor 214 can be communicatively connected to a computer readable medium that includes volatile or nonvolatile memory upon which computer readable medium is stored. The programmable processor 214 can access the computer readable medium and upon executing the computer readable code carries out the functions as described herein. The control circuit 212 can be any suitable control device for interpreting information from the wires 210, but is not limited to an engine control module (ECM), a controller, a fluid management control module, or any suitable data/information processing device, which may employ one or more software routines, as appropriate. In this example, the control circuit 212 is powered by any conventional power source, such as for example one or more batteries 63. The control circuit 212 is configured to supply an electrical current to the pair of wires 210 and to receive electrical current from the pair wires 210. However the control circuit 212 does not have to supply electrical current to the pair of wires 210; rather the noted electrical current could be directly provided by any other power source such a battery.

In use, when the qualified filter element 202 is installed in the filter housing 204, the plurality of wires 210 cuts the magnetic field 208 of the magnetic element 206 thereby modifying a current generated across the wires 210. The current on the wires 210 is monitored by the control circuit 212. A change in the current on the wires 210 alerts the control circuit 212 that the qualified filter element 202 is installed. Like the example in FIG. 1, the control circuit 212 can be programmed to control an output device 57 having warning lights 59, 61 and/or other conventional means for alerting an operator as to whether there is a qualified filter element 24 installed in the filter housing 26.

FIGS. 11C-11D depict another example of a filter system 220 wherein a plurality of magnetic elements 206 are spaced apart on the circumferential surface. The control circuit 50 has a plurality of input terminals A-D that are connected to respective pairs of wires 210. The orientation and location of the respective magnetic elements in the plurality 206 can be selected so that movement of the qualified filter element 202 with respect to the filter housing 204 (e.g. rotation during installation of the qualified filter element 202 into the filter housing 24) causes a current induced pulse that is detected by the control circuit 212 via the input terminals A-D. The control circuit 212 can be programmed to interpret the current induced pulse as a code and to compare the current induced pulse or code to a stored current induced pulse or code in the memory 216 to thereby verify that the filter element is a qualified filter element 202. The code can vary depending upon the location and orientation of the magnetic elements 206 in the plurality. In the example shown, the qualified fiber element 202 is turned clockwise during installation. This causes terminals A and B to generate a negative current signal that is read by the control circuit 212. Terminals C and D generate a positive current signal that is read by the control circuit 212. The memory 216 of the control circuit 212 contains a look-up table or other list that indicates that when this code or combination of positive and negative current signals are detected, the control circuit 212 should indicate via the output device 57 that a qualified filter element 202 has been installed. The control circuit 212 will not indicate that a qualified filter element 202 has been installed until this particular combination of positive and negative current signals are detected. Conversely, when the qualified filter element 202 is uninstalled, counterclockwise rotation of the qualified filter element 202 with respect to the filter housing 204 causes terminals A and B to generate a positive current signal and terminals C and D to generate a negative current signal. Again, the memory 216 of the control circuit 212 contains a look-up table or other list that indicates that when this combination of positive and negative current signals are detected, the control circuit 212 should indicate via the output device 57 that a qualified filter element 202 has been uninstalled Changing the location or orientation of the magnetic element 206 will change the corresponding current-induced pulse and thus change the code that is interpreted by the control circuit 212, allowing the manufacturer to tailor the noted code to thereby prevent counterfeiting.

Although only a few example examples have been described in detail above, those skilled in the art will readily appreciate that many modifications are possible in the example examples without materially departing from this invention. Accordingly, all such modifications are intended to be included within the scope of this disclosure as defined in the following claims. In the claims, means plus function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the inventors not to invoke 35 U.S.C. §112, paragraph six, for any limitations of any of the claims herein, except for those in which the claim expressly uses the words "means for" together with an associated function.

What is claimed is:

1. A filter assembly comprising:
a filter housing;
a qualified filter element;
a plurality of magnetic elements disposed on at least one of the filter housing and the qualified filter element, the plurality of magnetic elements each having a magnetic field;
a plurality of wires disposed on at least the other of the filter housing and the qualified filter element; and
a control circuit that is electrically coupled to the plurality of wires and that detects an electrical current in the plurality of wires;
wherein when the qualified filter element is installed in the filter housing, the plurality of wires cuts the magnetic field of at least one of the plurality of magnetic elements and thereby changes the electrical current in the plurality of wires;
wherein the control circuit determines that the qualified filter element is installed in the filter housing based on a change in the electrical current in the plurality of wires.

2. The filter assembly according to claim 1, wherein the current generated in the plurality of wires produces a current induced pulse and wherein the control circuit compares the current-induced pulse to a stored current-induced pulse to verify whether the qualified filter element is qualified.

3. The filter assembly according to claim 2, wherein changing the location of the plurality of magnetic elements on the filter housing changes the current-induced pulse.

4. The filter assembly according to claim 2, wherein changing the orientation of the plurality of magnetic elements on the filter housing changes the current-induced pulse.

5. The filter assembly according to claim 1, wherein the qualified filter element has a circumferential outer surface and wherein magnetic elements in the plurality of magnetic elements are spaced apart around the circumferential outer surface.

6. The filter assembly according to claim 5, wherein the qualified filter element is installed in the filter housing by rotating the qualified filter element with respect to the filter housing so that the plurality of magnetic elements are rotated past the plurality of wires during installation.

7. A method of identifying a qualified filter element in a filter assembly having a filter housing, the method comprising:
providing a plurality of magnetic elements on at least one of the qualified filter element and the filter housing, the plurality of magnetic elements comprising a magnetic field;
providing a plurality of wires on at least the other of the qualified filter element and the filter housing;
installing the qualified filter element into the filter housing:

sensing with a control circuit an electrical current along the plurality of wires; and identifying with the control circuit that the qualified filter element is installed in the filter housing when the electrical current across the wires changes.

8. The method according to claim 7, comprising rotating the qualified filter element with respect to the filter housing so that the plurality of magnetic elements passes by the plurality of wires during rotations.

9. The method according to claim 8, comprising interpreting with the control circuit a current induced pulse caused by the current generated in the plurality of wires during said rotation and comparing the current induced pulse to a stored code to verify that the qualified filter element is qualified.

10. The method according to claim 9, comprising changing the location of the plurality of magnetic elements to change the current induced pulse.

11. The method according to claim 9, comprising changing the orientation of the plurality of magnetic elements to change the current induced pulse.

* * * * *